(12) United States Patent
Huang et al.

(10) Patent No.: US 12,427,526 B2
(45) Date of Patent: Sep. 30, 2025

(54) SAMPLE COLLECTION DEVICE

(71) Applicant: Delta Electronics, Inc., Taoyuan (TW)

(72) Inventors: Song-Bin Huang, Taoyuan (TW); Jing Geng, Taoyuan (TW); Quanke Long, Taoyuan (TW); Xiaozhi Zhao, Taoyuan (TW); Hsiu-Hui Chang, Taoyuan (TW)

(73) Assignee: Delta Electronics, Inc., Taoyuan (TW)

( * ) Notice: Subject to any disclaimer, the term of this patent is extended or adjusted under 35 U.S.C. 154(b) by 796 days.

(21) Appl. No.: 17/741,287

(22) Filed: May 10, 2022

(65) Prior Publication Data

US 2022/0362762 A1 Nov. 17, 2022

Related U.S. Application Data

(60) Provisional application No. 63/188,746, filed on May 14, 2021.

(30) Foreign Application Priority Data

Mar. 23, 2022 (CN) .......................... 202210290795.9

(51) Int. Cl.
*A61B 10/00* (2006.01)
*B01L 3/00* (2006.01)
(Continued)

(52) U.S. Cl.
CPC ............ *B01L 7/52* (2013.01); *A61B 10/0045* (2013.01); *A61B 10/0096* (2013.01);
(Continued)

(58) Field of Classification Search
CPC ........ B01L 7/52; B01L 3/0227; B01L 3/0234; B01L 3/5029; B01L 2300/021;
(Continued)

(56) References Cited

U.S. PATENT DOCUMENTS 7,122,157 B2  10/2006  Stevens et al.
8,728,414 B2   5/2014  Beach et al.
(Continued)

FOREIGN PATENT DOCUMENTS

CN  108478223 A   9/2018
CN  209495879 U  10/2019
(Continued)

OTHER PUBLICATIONS

Xing Yading, Effects of different specimen sampling methods on the positive detection rate of hand, foot and mouth disease in children, Today Nurse, May 2016, No. 5.

*Primary Examiner* — John Mcguirk
(74) *Attorney, Agent, or Firm* — KIRTON McCONKIE; Evan R. Witt (57) ABSTRACT

A sample collection device includes a tube, a closure and a partitioning member. The tube includes an opening and is used to receive a sampling swab. The closure is engaged with the tube for enclosing the opening. The partitioning member is disposed in the tube and includes a blocking portion and a position-limiting portion. The blocking portion is disposed close to the opening and covers a portion of the opening so as to leave another uncovered portion as an entrance for passing the sampling swab therethrough. The position-limiting portion is connected with the blocking portion and extended into the tube, so as to limit the sampling swab in a space corresponding to the entrance inside the tube after the sampling swab passes through the entrance.

11 Claims, 7 Drawing Sheets

(51) Int. Cl.
*B01L 3/02* (2006.01)
*B01L 7/00* (2006.01)
*B03C 1/01* (2006.01)
*B03C 1/28* (2006.01)
*G01N 1/02* (2006.01)
*G01N 35/00* (2006.01)
*G01N 35/10* (2006.01)

(52) U.S. Cl.
CPC ........... *B01L 3/0227* (2013.01); *B01L 3/0234* (2013.01); *B01L 3/5029* (2013.01); *B03C 1/01* (2013.01); *B03C 1/288* (2013.01); *G01N 1/02* (2013.01); *G01N 35/1002* (2013.01); *B01L 2300/021* (2013.01); *B01L 2300/0829* (2013.01); *B01L 2300/0832* (2013.01); *B01L 2300/1805* (2013.01); *G01N 2001/028* (2013.01); *G01N 35/0098* (2013.01)

(58) Field of Classification Search
CPC ..... B01L 2300/0829; B01L 2300/0832; B01L 2300/1805; B01L 3/50853; B01L 2300/042; B01L 2300/0609; B01L 2300/0858; A61B 10/0045; A61B 10/0096; B03C 1/01; B03C 1/288; B03C 1/284; B03C 1/286; B03C 2201/18; B03C 2201/26; G01N 1/02; G01N 35/1002; G01N 35/0098; G01N 2001/028; Y02A 50/30; Y02W 90/10; B65D 41/04; C12M 23/06; C12M 23/34; C12M 23/38; C12M 33/04

See application file for complete search history.

(56) References Cited

U.S. PATENT DOCUMENTS

| | | | |
|---|---|---|---|
| 11,040,340 B1 | 6/2021 | Moore et al. | |
| 2005/0013742 A1* | 1/2005 | Shaw | B65D 41/0485 422/400 |
| 2009/0176301 A1* | 7/2009 | Oldenburg | C12M 27/02 435/297.1 |
| 2020/0408654 A1* | 12/2020 | Strnad | G01N 1/44 |

FOREIGN PATENT DOCUMENTS

| | | | | |
|---|---|---|---|---|
| CN | 111839607 A | | 10/2020 | |
| CN | 111849732 A | | 10/2020 | |
| CN | 211904777 U | | 11/2020 | |
| CN | 212630804 U | * | 3/2021 | ............ A61B 10/00 |
| CN | 213447119 U | | 6/2021 | |
| CN | 214088499 U | * | 8/2021 | |
| CN | 113528303 A | | 10/2021 | |
| JP | 2008101971 A | | 5/2008 | |
| TW | M532281 U | | 11/2016 | |
| WO | WO-2021209755 A1 | * | 10/2021 | .......... B01L 3/50825 |

* cited by examiner

SAMPLE COLLECTION DEVICE

CROSS-REFERENCE TO RELATED APPLICATION

This application claims the benefit of U.S. Provisional Application No. 63/188,746 filed on May 14, 2021 and entitled "AUTOMATIC NUCLEIC ACID PROCESSING WORKSTATION". This application also claims priority to China Patent Application No. 202210290795.9 filed on Mar. 23, 2022. The entireties of the above-mentioned patent application are incorporated herein by reference for all purposes.

FIELD OF THE INVENTION

The present disclosure relates to a sample collection device, and more particularly to a sample collection device suitable for an automated apparatus.

BACKGROUND OF THE INVENTION

The detections of many diseases (such as respiratory diseases, reproductive tract diseases, urinary tract diseases, and other related diseases) are sampled via a sampling swab, e.g., a flocked swab or a cotton swab. After sampling, the sampling swab is put into a sample collection device, so that the head portion of the sampling swab can be immersed in the preservation liquid contained in the sample collection device for releasing the sample adhered thereon. The sampling swab is also broken off for being accommodated in the sample collection device. Then, the sample collection device is sealed to complete the sampling procedure.

Afterwards, the sample collection device with the sampling swab is transported to the laboratory for detection. For example, a pipet (such as a micropipette) is used to draw up the liquid with the sample in the sample collection device for performing the nucleic acid amplification and analysis. Because the sampling swab is placed in the sample collection device in a random angle, the entering of the pipet is easily blocked thereby, which results in that the operator has to adjust the position of the sampling swab manually for ensuring a smooth entering of the pipet.

In recent years, the detection demand for respiratory infectious diseases has increased greatly, and the demand for using the automated apparatus to process the sample detection has also increased. When the pipet of the automated apparatus enters the sample collection device, the problem described above also occurs and causes an interruption of the automated procedure due to being blocked by the sampling swab. Accordingly, an additional step of manually adjusting or removing the sampling swab needs to be added before starting the automated procedure, which increases not only the labor cost, but also the risks of sample contamination and human infection.

Therefore, there is a need of providing a sample collection device suitable for an automated apparatus.

SUMMARY OF THE INVENTION

An object of the present disclosure is to provide a sample collection device which can position a sampling swab therein in a restricted space so as to ensure the entering of an external pipet without being blocked.

An additional object of the present disclosure is to provide a sample collection device which divides the inner space into two portions by disposing a partitioning member therein for respectively receiving a sampling swab and an external pipet, and the partitioning member also provides a function of preventing misplacing of the sampling swab.

A further object of the present disclosure is to provide a sample collection device having a tube and a closure designed for an automated opening and closing procedure.

In accordance with an aspect of the present invention, a sample collection device is provided. The sample collection device includes a tube having an opening for receiving a sampling swab, a closure engaged with the tube for enclosing the opening, and a partitioning member disposed in the tube. The partitioning member includes a blocking portion disposed close to the opening for covering a portion of the opening so as to leave another uncovered portion of the opening as an entrance for passing the sampling swab therethrough, and a position-limiting portion connected with the blocking portion and extended into the tube for limiting the sampling swab in a space corresponding to the entrance inside the tube after the sampling swab passes through the entrance.

In an embodiment, the partitioning member further includes a bending mechanism disposed between the blocking portion and the position-limiting portion, so that the blocking portion is able to bend toward the position-limiting portion for exposing the covered portion of the opening when an external pipet enters the tube.

In an embodiment, the bending mechanism includes a bending line for guiding a bending of the blocking portion.

In an embodiment, the bending mechanism includes a bending gap for providing a deformation space for the blocking portion to bend toward the position-limiting portion.

In an embodiment, the position-limiting portion further includes a hollow portion for receiving a portion of the blocking portion in a bent state.

In an embodiment, the position-limiting portion is a sheet structure having a length extended in a direction substantially parallel to a longitudinal direction of the tube.

In an embodiment, a length of the position-limiting portion is less than a length of the tube in the longitudinal direction, and a bottom edge of the position-limiting portion is a distance away from a bottom portion of the tube.

In an embodiment, the blocking portion is a plate structure, and the blocking portion and the position-limiting portion are substantially perpendicular to each other.

In an embodiment, the sample collection device further includes two engaging elements fixed in the tube and abutting against the position-limiting portion so as to position the partitioning member within the tube.

In an embodiment, the tube includes an orientation structure for providing an orientation function as the tube is placed vertically.

In an embodiment, the closure includes a first end and a second end, the first end is screwed with the opening of the tube and the second end is screwed with an automated opening and closing device, and the first end and the second end have opposite screwing directions.

In an embodiment, the tube has a protrusion disposed on an outer sidewall near the opening, and the closure has a recess corresponding to the protrusion so as to provide a notification as a screwing between the closure and the tube is completed.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for a purpose of illustration and description only. It is not intended to be exhaustive or to be limited to the precise form disclosed.

Figure 1:
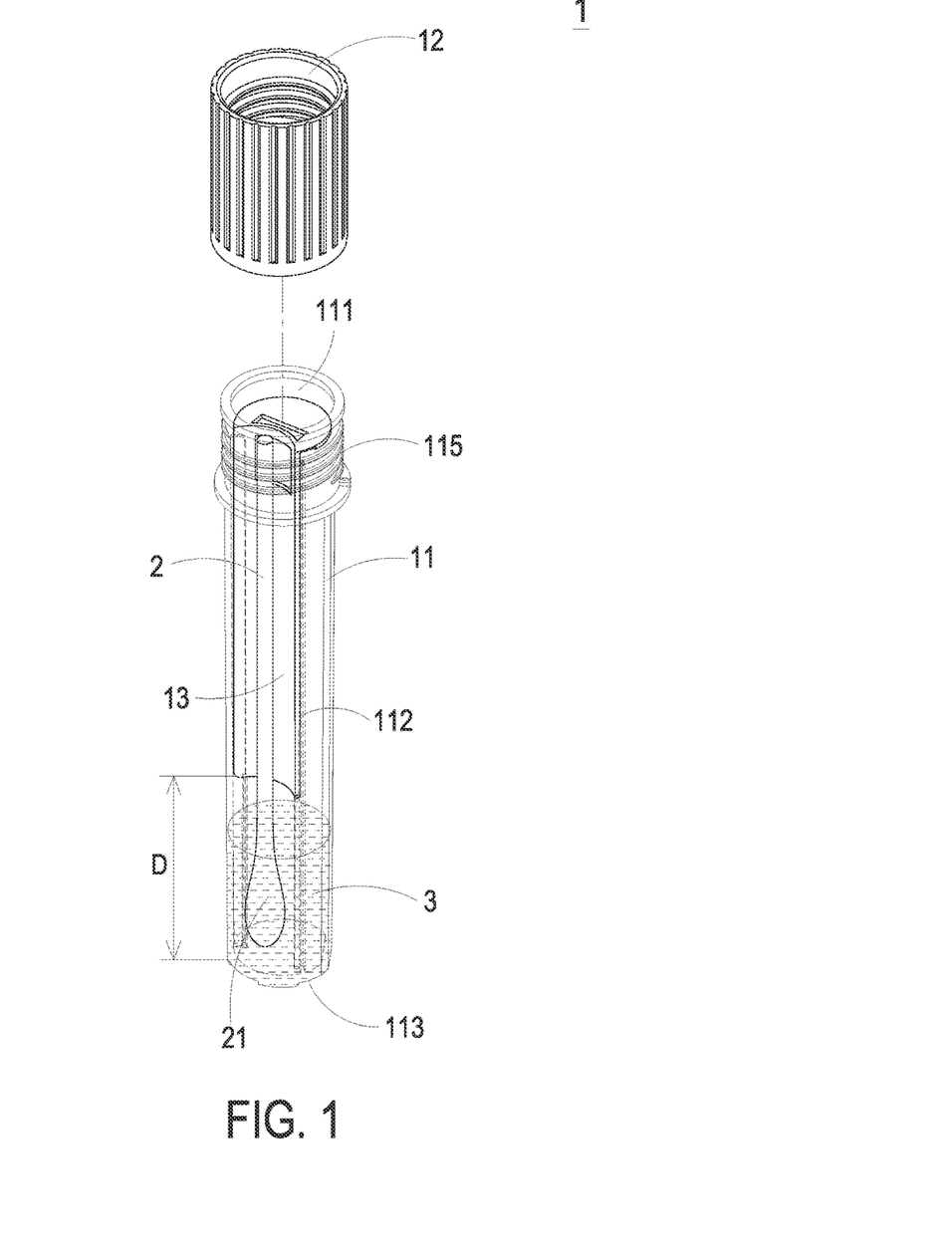
FIG. 1 is a schematic view showing a sample collection device according to an embodiment of the present disclosure.

Please refer to FIG. 1, which is a schematic view showing a sample collection device according to an embodiment of the present disclosure. A sample collection device 1 includes a tube 11, a closure 12 and a partitioning member 13. The tube 11 has an opening 111, and a sampling swab 2 (such as a flocked swab or a cotton swab) can pass through the opening 111 and be received in the tube 11. The closure 12 is engaged with the tube 11 for enclosing the opening 111, so as to keep the sampling swab 2 in the tube 11, prevent the liquid 3 (e.g., sample preservation liquid) in the tube 11 from leaking out, and avoid sample contamination. In an embodiment, the opening 111 is a circular opening for facilitating a screwing engagement with the closure 12 so as to achieve an effective enclosure. Further, preferably but not exclusively, the tube 11 can be formed to have a cylindrical shape, a cylinder-like shape or other columnar shapes. Moreover, a sealing element (not shown), such as a rubber ring or a silicon ring, can be disposed in the closure 12 for further preventing the liquid 3 from leakage.

Figure 2A:
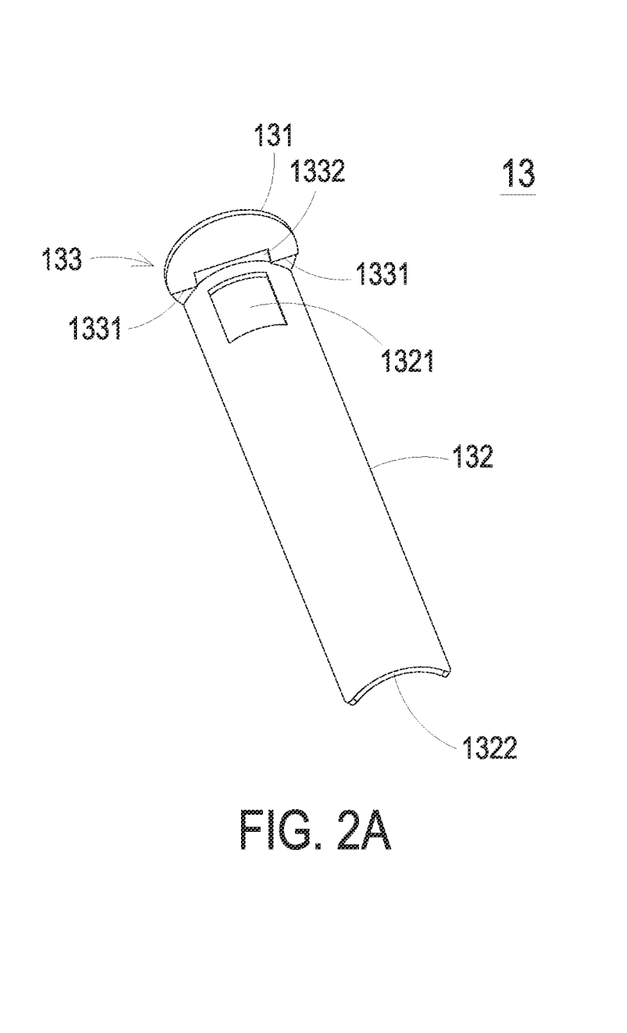
FIG. 2A is a schematic view showing a partitioning member according to an embodiment of the present disclosure.
Figure 2B:
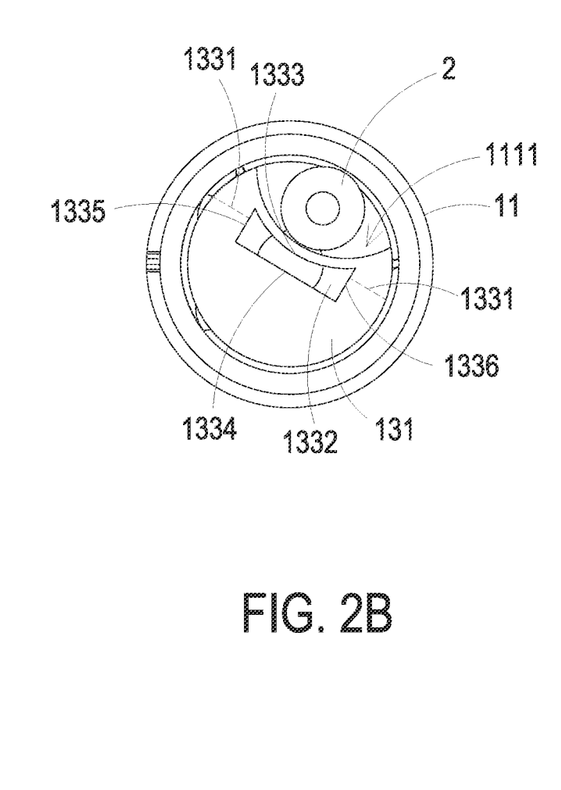
FIG. 2B is a top view from an opening of a tube of the sample collection device shown in FIG. 1.

Please refer to FIG. 1 and FIGS. 2A-2B. FIG. 2A is a schematic view showing the partitioning member 13 according to an embodiment of the present disclosure, and FIG. 2B is a top view from the opening 111 as the partitioning member 13 is disposed in the tube 11. The present disclosure utilizes the partitioning member 13 disposed in the tube 11 to solve the problems encountered in the prior art. The partitioning member 13 includes a blocking portion 131 and a position-limiting portion 132. The blocking portion 131 is disposed in the tube 11 close to the opening 111 for covering a portion of the opening 111 and leaving another uncovered portion of the opening 111. Thus, the blocking portion 131 is substantially parallel to a section of the opening 111, namely substantially perpendicular to a longitudinal direction of the tube 11, so as to achieve a blocking effect. Accordingly, in a preferred embodiment, the blocking portion 131 is a plate structure, such as a blocking sheet or a blocking plate, which has a shape substantially matching to an inner edge of the covered portion of the opening 111. The blocking portion 131 is not limited to the aforementioned structure, and may also be any structure capable of covering a portion of the opening 111. The uncovered portion of the opening 111 is utilized as an entrance 1111 for the sampling swab 2 to enter the tube 11. In other words, through disposing the blocking portion 131, the opening 111 is divided into two portions in which one portion is covered and the other uncovered portion serves as the entrance 1111, so that when the closure 12 is removed, it can be seen that the opening 111 is shank to leave only the entrance 1111. Thus, the operator can put the sampling swab 2 into the tube 11 through the entrance 1111 naturally.

On the other hand, the position-limiting portion 132 is connected with the blocking portion 131, e.g., in a direction substantially perpendicular to the blocking portion 131, and extended into the tube 11. Through the position-limiting portion 132, the position of the sampling swab 2 can be restricted after entering the tube 11 through the entrance 1111. More specifically, different from the prior art in which the sample swab is rested in a random angle, when the sampling swab 2 of the present disclosure enters the tube 11, it can be restricted in a space between the position-limiting portion 132 and the tube 11, namely, the sampling swab 2 can be restricted in a space inside the tube 11 corresponding to the entrance 1111.

In an embodiment, the position-limiting portion 132 is a sheet structure having a length extended in a direction substantially parallel to the longitudinal direction of the tube 11, so as to keep the sampling swab 2 in a vertical pose as much as possible and thus reduce an area occupied by the sampling swab 2 in the section perpendicular to the longitudinal direction of the tube 11. In other words, an area occupied by the blocking portion 131 in the section, which is also the space for an external pipet (such as a pipet of an automated apparatus) to pass through, is maximized as much as possible. Moreover, a sectional shape of the sheet structure of the position-limiting portion 132 in a direction perpendicular to the longitudinal direction thereof can be different in demands. The boundary of the entrance 1111 is collaboratively defined by the position-limiting portion 132 and the tube 11, namely it is formed by the sheet structure intersecting with the tube 11 in a width direction. In the case that the tube 11 has a cylindrical shape or cylinder-like shape, at least a portion of the boundary of the entrance 1111 is constituted by a portion of the tube 11 which has an arc or arc-like shape. Thus, only if the space collaboratively defined by the position-limiting portion 132 and the tube 11 is sufficient to receive the sampling swab 2, the sectional shape of the sheet structure is not limited. In a preferred embodiment, because a head portion 21 of the sampling swab 2 usually has a ball shape or a ball-like shape, the sectional shape of the sheet structure can also have an arc shape for cooperating with the arc or arc-like shape of the tube 11 so as to form the entrance 1111 in a circular-like shape, but not limited thereto.

In an embodiment, for making the head portion 21 of the sampling swab 2, where the sample is mainly adhered, well mixed with the liquid 3 in the sample collection device 1, a length of the position-limiting portion 132 is designed to be less than a length of the tube 11 in a longitudinal direction, and a bottom edge of the position-limiting portion 132 is a distance D away from a bottom portion 113 of the tube 11. In other words, the position-limiting portion 132 is not extended to the bottom portion 113, namely, an inner space of the tube 11 near the bottom portion 113 is not divided into two portions. Therefore, the sample adhered to the head portion 21 can be released to and fully mixed with the liquid 3 contained in different areas of the tube 11 without being blocked by the position-limiting portion 132, and the external pipet can enter the tube 11 to draw up the liquid 3 with the sample near the bottom portion 113, which is beneficial for improving the accuracy of the detection result of the sample. In an embodiment, the length of the position-limiting portion 132 is substantially larger than a half of the length of the tube, such as ranged between one-half and two-thirds, but not limited thereto.

In an embodiment, in order to make the external pipet enter the tube 11 smoothly for drawing up the liquid 3 with the sample, the partitioning member 13 further includes a bending mechanism 133 disposed between the blocking portion 131 and position-limiting portion 132. For entering the tube 11, the pipet should contact and press down the blocking portion 131, and the bending mechanism 133 makes the blocking portion 131 be able to bend toward the position-limiting portion 132 due to a force applied by the pipet when entering the tube 11, and expose the originally covered portion of the opening 111. Accordingly, the pipet can smoothly enter the tube 11 and draw up the liquid 3 with the sample.

However, as described above, the sectional shape of the position-limiting portion 132 can be different depending on demands, so a borderline between the blocking portion 131 and the position-limiting portion 132 may correspondingly have a different shape. For example, the borderline is an arc borderline due to the position-limiting portion 132 is an arc sheet structure. In this situation, it may become not easy to bend the blocking portion 131 toward the position-limiting portion 132.

Figure 3:
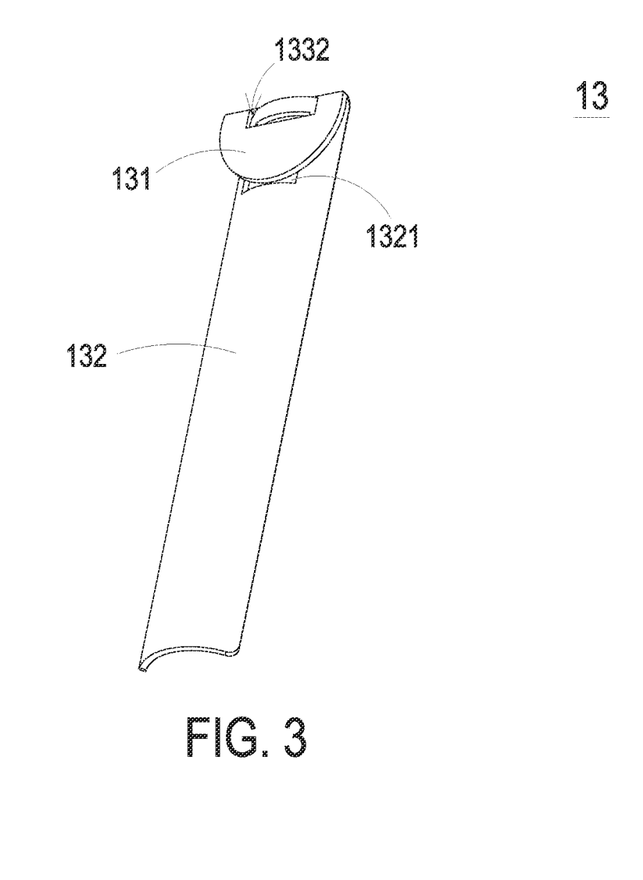
FIG. 3 is a schematic view showing the partitioning member as a blocking portion is bent toward a position-limiting portion according to an embodiment of the present disclosure.

Therefore, in order to effectively achieve the bending of the blocking portion 131, the bending mechanism 133 is provided. Please refer to FIGS. 2A-2B and FIG. 3. FIG. 3 is a schematic view showing the partitioning member 13 as the blocking portion 131 is bent toward the position-limiting portion 132. The bending mechanism 133 includes a bending line 1331 and a bending gap 1332. The bending line 1331 is used to guide the bending of the blocking portion 131. Particularly, the bending line 1331 is a pre-folded line on the blocking portion 131 close to the position-limiting portion 132 for the blocking portion 131 to follow as the bending occurs. The bending gap 1332 is a void located between the blocking portion 131 and the position-limiting portion 132. The bending gap 1332 includes a first edge 1333 adjacent to the position-limiting portion 132, a second edge 1334 opposite to the first edge 1333, and a third edge 1335 and a fourth edge 1336 respectively connecting the first edge 1333 and the second edge 1334.

In order to maximize the space for passing the external pipet therethrough, the bending line 1331 is preferably as close as possible to the position-limiting portion 132, namely close to the arc borderline. However, since the arc sheet structure of the position-limiting portion 132 may cause difficulty in bending, the bending gap 1332 is further designed for providing a deformation space so as to facilitate the bending of the blocking portion 131. In an embodiment, the bending gap 1332 is adjacent to the arc borderline, wherein the first edge 1333 is an arc substantially corresponding to the arc borderline, and the bending line 1331 is extended from the third edge 1335 and the fourth edge 1336 oppositely to the edge of the blocking portion 131. In other words, the bending line 1331 passes through the bending gap 1332 and the bending of the blocking portion 131 occurs at two opposite sides of the bending gap 1332. More specifically, because the bending gap 1332 provides the deformation space needed by the blocking portion 131 as bending toward the position-limiting portion 132, no matter what shape the borderline between the blocking portion 131 and the position-limiting portion 132 is and where the bending line 1331 is, the bending can be executed smoothly without deforming the blocking portion 131 and/or the position-limiting portion 132.

In an embodiment, for eliminating the possibility of the bent blocking portion 131 to block the entering of the external pipet, a hollow portion 1321 is further provided on the position-limiting portion 132 near a top edge thereof for receiving at least a portion of the bent blocking portion 131, so as to ensure the blocking portion 131 in a bent state to be not protruded out of the curved surface of the position-limiting portion 132. A distance from a top edge of the hollow portion 1321 to the top edge of the position-limiting portion 132 is less than a minimum height of the bending gap 1332 (namely the shortest distance between the first edge 1333 and the second edge 1334). In other words, when the blocking portion 131 is bent along the bending line 1331, the bending gap 1332 provides the space for a portion between the top edge of the hollow portion 1321 and the top edge of the position-limiting portion 132 to pass through. Further, a distance from a bottom edge to the top edge of the hollow portion 1321 is larger than a linear distance between the second edge 1334 of the bending gap 1332 and the edge of the blocking portion 131, so that the bent blocking portion 131 can be received in the hollow portion 1321. Thus, the blocking portion 131 in the bent state can be at a location not protruded out of the curved surface of the position-limiting portion 132, and the external pipet can enter the tube 11 smoothly for drawing up the liquid 3.

Consequently, through the cooperation between the bending mechanism 133 and the hollow portion 1321, it is able to bend the blocking portion 131 to provide the maximum space for passing the external pipet therethrough but still keep the position-limiting portion 132 being an arc sheet structure and the blocking portion 131 being a plate structure.

After the external pipet leaves the tube 11, since the force causing the blocking portion 131 to bend is disappeared, the blocking portion 131 returns to the original position, namely, the position covering the portion of the opening 111. Accordingly, it is preferable that the partitioning member 13 is made of an elastic material, such as but not limited to plastic, so as to ensure the bending and the rebound of the blocking portion 131 in response to the entering and leaving of the pipet.

Figure 4A:
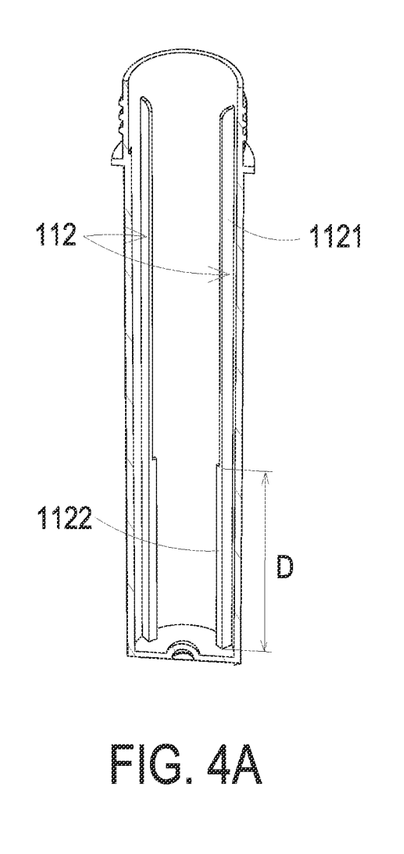
FIG. 4A is a sectional view of the tube in a longitudinal direction according to an embodiment of the present disclosure.
Figure 4B:
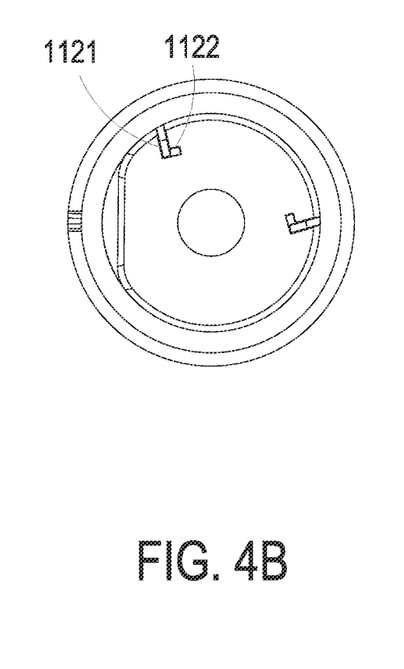
FIG. 4B is a top view from an opening of the tube according to an embodiment of the present disclosure.
Figure 4C:
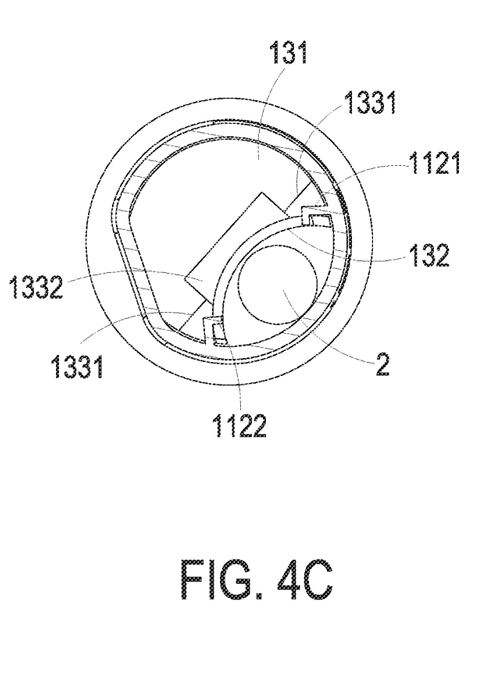
FIG. 4C is a perspective view of the tube from the bottom thereof as the partitioning member is disposed therein according to an embodiment of the present disclosure.

Please refer to FIGS. 4A-4C. FIG. 4A is a sectional view of the tube 11 in the longitudinal direction according to an embodiment of the present disclosure, FIG. 4B is a top view from an opening 111 of the tube 11 according to an embodiment of the present disclosure, and FIG. 4C is a perspective view of the tube 11 from the bottom thereof as the partitioning member 13 is disposed therein according to an embodiment of the present disclosure. In an embodiment, there are two engaging elements 112 fixed in the tube 11, and through mutual abutting engagements between the two engaging elements 112 and the position-limiting portion 132, the partitioning member 13 can be positioned in the tube 11. The two engaging elements 112 are fixed on the inner sidewall of the tube 11 in a manner of parallel to the longitudinal direction of the tube 11 with a distance separated from each other. Each engaging element 112 is protruded from the inner sidewall toward the interior of the tube 11 to form a first engaging portion 1121. For example, each first engaging portion 1121 is a strip bulge elongated along the longitudinal direction of the tube 11 from a location near the opening 111 to the bottom portion 113. Two ends of the position-limiting portion 132 in the width direction are respectively abut against each the first engaging portion 1121 and the tube 11, so as to position the partitioning member 13 within the tube 11. In other words, through the abutting engagements among the first engaging portions 1121, the tube 11 and the position-limiting portion 132, the partitioning member 13 is fixed, and the covered portion covered by the blocking portion 131 and the entrance 1111 defined by the position-limiting portion 132 and the tube 11 for passing the sampling swab 2 therethrough are also fixed.

The distance between the two engaging elements 112 is decided by the position-limiting portion 132. That is, since the function of the two engaging elements 112 is to position the partitioning member 13 by abutting against the position-limiting portion 132, the locations of the two engaging elements 112 and the protruding directions of the two first engaging portions 1121 may be different in response to the different shape of the position-limiting portion 132. For example, in a preferable embodiment, the locations and the protruding directions of the two first engaging portions 1121 are designed to be able to just apply forces to the two ends of the arc position-limiting portion 132 and thus cause the arc position-limiting portion 132 to generate a resilience force, thereby achieving the effect of fixing. Preferably but not exclusively, the position-limiting portion 132 is made of an elastic material, such as the plastic, for enhancing the fixing effect.

Furthermore, a second engaging portion 1122 is further formed at a lower portion of each of the first engaging portions 1121. Each the second engaging portion 1122 is extended from and substantially perpendicular to the first engaging portion 1121, and a top edge of each the second engaging portion 1122 contacts the bottom edge of the position-limiting portion 132. More specifically, the second engaging portions 1122 support the position-limiting portion 132 from below and thus simultaneously keep the bottom edge of the position-limiting portion 132 being higher than the bottom portion 113 of the tube 11. Thus, the bottom edge of the position-limiting portion 132 and the bottom portion 113 of the tube 11 are separated by the height of the second engaging portion 1122 which is the distance D (as shown in FIG. 1) between the bottom edge 1322 of the position-limiting portion 132 and the bottom portion 113 of the tube 11, as described above.

Certainly, since the function of the second engaging portions 1122 is to support the position-limiting portion 132 from below, only if the supporting can be achieved, there is no limitation to the protruding directions thereof from the first engaging portions 1121. For example, the protruding directions of the first engaging portion 1121 and the second engaging portion 1122 can be perpendicular or parallel to each other, or intersected at other angles. Moreover, the first engaging portion 1121 and the second engaging portion 1122 can be formed integrally or to be independent components without limitation. In addition, depending on the manufacturing process, the partitioning member 13 and the tube 11 also can be formed integrally or to be two independent components without limitation.

On the other hand, since the sample collection device 1 of the present disclosure includes the partitioning member 13 therein, i.e., the inner space of the tube 11 is divided into two portions, when plural sample collection devices 1 are processed at the same time via an automated apparatus, for example, plural sample collection devices 1 are disposed in a tube rack for a batch processing via the automated apparatus, if all the sample collection devices 1 can be positioned in an identical direction, the operation of the automated apparatus will not be interrupted due to different partitioning directions in the sample collection devices 1. In other words, it is preferable that when plural sample collection devices 1 are placed vertically in the tube rack, the positions and orientations of the position-limiting portions 132 for the plural sample collection devices 1 can be identical relative to the tube rack, thereby ensuring all pipets can enter each the sample collection device 1 smoothly without being blocked.

Figure 5A:
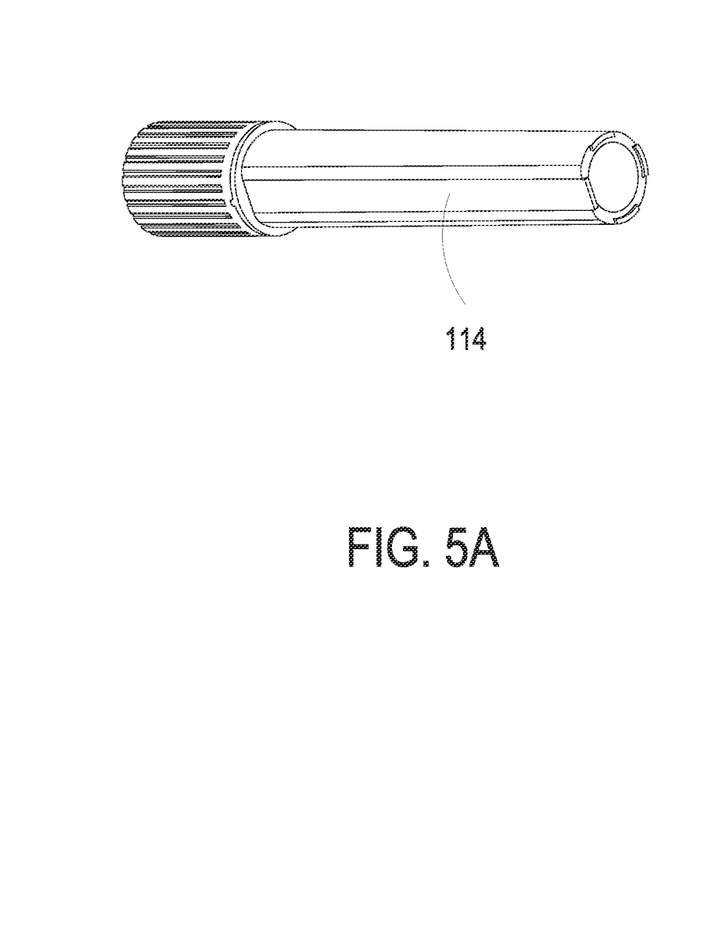
FIG. 5A is a schematic view showing the sample collection device according to an embodiment of the present disclosure.
Figure 5B:
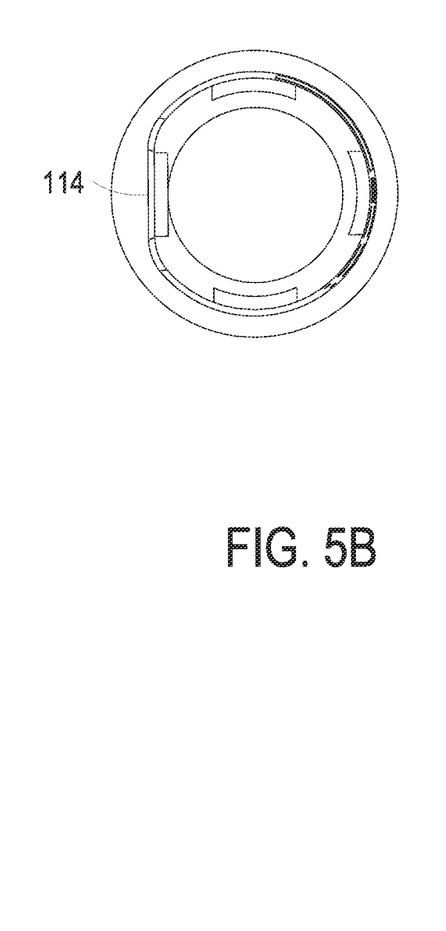
FIG. 5B is a bottom view of the sample collection device according to an embodiment of the present disclosure.

Please refer to FIGS. 5A-5B. FIG. 5A is a schematic view showing the sample collection device 1 according to an embodiment of the present disclosure, and FIG. 5B is a bottom view of the sample collection device 1 according to an embodiment of the present disclosure. The tube further includes an orientation structure 114 which forms an unsymmetrical portion on the tube 11 and provides an orientation function as the tube 11 is placed vertically. For example, the orientation structure 114 can be a shrink of the sidewall on the cylinder or cylinder-like tube 11, so as to cause the section of the tube 11 perpendicular to the longitudinal direction thereof to have an unsymmetrical shape. As such, by matching the shape of each slot of the tube rack with the unsymmetrical portion of the tube 11, the orientation of the sample collection device 1 can be achieved.

Figure 6A:
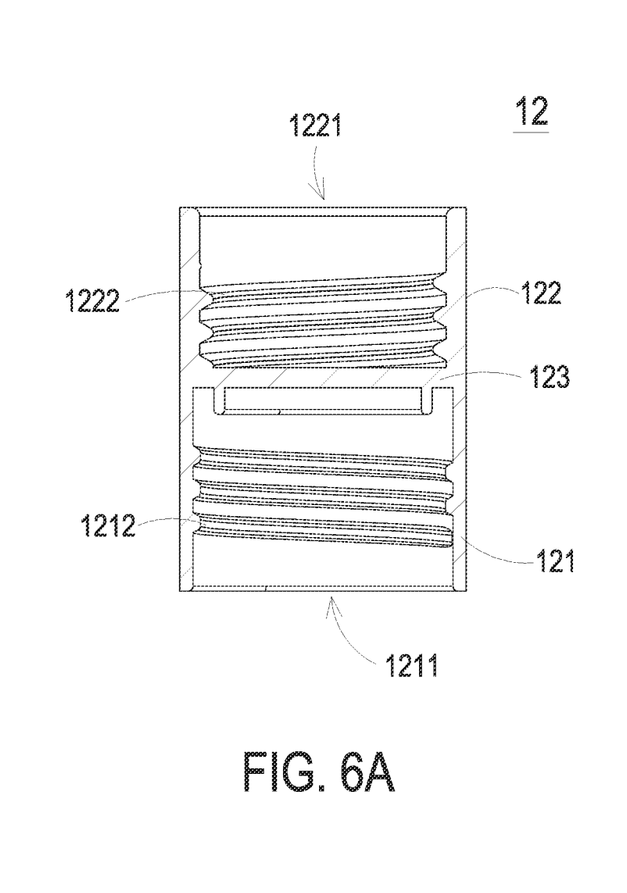
FIG. 6A is a sectional view of a closure of the sample collection device in the longitudinal direction according to an embodiment of the present disclosure.
Figure 6B:
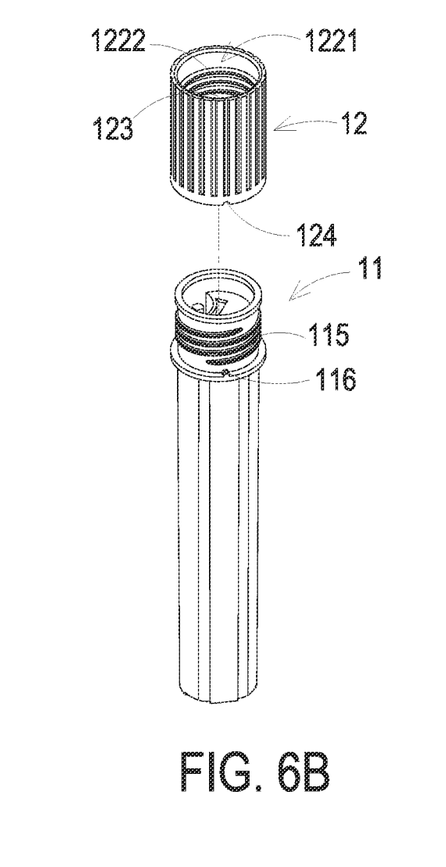
FIG. 6B is a schematic view showing the closure and the tube according to an embodiment of the present disclosure.

In addition, for minimizing the manual operation, the sample collection device 1 of the present disclosure is further designed for automated opening and closing processes. Please refer to FIGS. 6A-6B. FIG. 6A is a sectional view of the closure 12 in the longitudinal direction according to an embodiment of the present disclosure, and FIG. 6B is a schematic view showing the closure 12 and the tube 11 according to an embodiment of the present disclosure. The closure 12 includes a first end 121, a second end 122 and a partition 123, wherein the first end 121 has a first opening 1211 and a first thread 1212, the second end has a second opening 1221 and a second thread 1222, and the partition 123 is disposed between the first end 121 and the second end 122. That is, the first end 121 and the second end 122 are respectively disposed at opposite sides of the partition 123, and the first opening 1211 and the second opening 1221 are facing opposite directions.

The first thread 1212 has a first screwing direction and the second thread 1222 has a second screwing direction, and the first screwing direction is opposite to the second screwing direction. For example, if the first screwing direction is a clockwise direction, then the second screwing direction is a counterclockwise direction. Further, the first end 121 is screwed with a thread 115 which is near the opening 111 of the tube 11 through the first thread 1212, namely the tube 11 has the thread 115, which is corresponding to the first thread 1212, on the outer sidewall thereof near the opening 111. The second end 122 is used to screw with an automated opening and closing device.

The automated opening process is as follows. In the case that the closure 12 has been screwed with the tube 11 via the first end 121 in the first screwing direction, the automated opening and closing device is first screwed with the second thread 1222 of the second end 122 of the closure 12 in the second screwing direction (e.g., the counterclockwise direction). Then, since the first screwing direction (e.g., the clockwise direction) of the first thread 1212 is opposite to the second screwing direction (e.g., the counterclockwise direction) of the second thread 1222, if the automated opening and closing device keeps screwing in the same direction (e.g., the counterclockwise direction) after being screwed tightly with the second thread 1222, the whole closure 12 will therefore be rotated in the second screwing direction (e.g., the counterclockwise direction) which is opposite to the first screwing direction (e.g., the clockwise direction). Thus, the first end 121 of the closure 12 and the tube 11 can be disengaged.

The automated closing process is as follows. In the case that the closure 12 has been screwed with the automated opening and closing device via the second end 122, the automated opening and closing device screws the closure 12 in the first screwing direction (e.g., the clockwise direction) for engaging the first thread 1212 of the first end 121 with the thread 115 of the tube 11. When the automated opening and closing device is screwed with the thread 115 tightly and then keeps screwing in the same direction (e.g., the clockwise direction), since the closure 12 has been locked and stops rotating, only the automated opening and closing device continues the screwing in the first screwing direction (e.g., the clockwise direction) which is opposite to the second screwing direction (e.g., the counterclockwise direction). Thus, the second end 122 of the closure 12 and the automated opening and closing device can be disengaged.

Notably, the premise for performing the automated opening and closing processes is that the tube 11 of the sample collection device 1 can substantially remain stationary during screwing. This can be achieved by the matching between the shapes of the orientation structure 114 and the corresponding tube rack, as described above. Therefore, the matching facilitates not only the entering of the pipet, but also the performing of the automated opening and closing processes, thereby the manual operation involved for the automated operation procedure can be minimized.

Moreover, for notifying the operator the screwing between the closure 12 and the thread 115 of the tube 11 is completed, a protrusion 116 is further provided on the outer sidewall of the tube 11 near the opening 111 and a recess 124 is provided on the closure 12 correspondingly. Thus, when the screwing of the closure 12 is ended, the protrusion 116 is simultaneously snapped in the recess 124 for providing a notification. For example, the hand performing the screwing can feel the pause, and/or a snap sound can be heard, so that the operator can recognize the screwing of the closure 12 is completed.

Furthermore, in an embodiment, the sample collection device 1 has one or more barcodes (not shown) disposed on the tube 11 for identifying and tracking the sample. For example, a one-dimensional barcode can be disposed on the outer sidewall of the tube 11, so that by operating the barcode scanner, the information of the subject and the sample collection device 1 can be read rapidly. Alternatively, a two-dimensional barcode can be disposed at the bottom of the tube 11, so that the sample collection device 1 can be automatically and rapidly recognized by the automated apparatus and the information can be introduced for being used in the further processing procedures, thereby improving the detection efficiency.

In conclusion, the present disclosure provides the sample collection device whose inner space is divided into two portions through disposing the partitioning member therein for respectively receiving the sampling swab and providing the space for passing the external pipet therethrough. The position-limiting portion of the partitioning member can keep the sampling swab in a substantially vertical pose closing to the sidewall of the tube, so as to maximize the space for passing the external pipet therethrough, and thus, the pipet of the automated apparatus will not be blocked by the sampling swab rested in a random angle as described in the prior art anymore and also the automated apparatus will not be interrupted thereby. Further, the blocking portion of the partitioning member which covers a portion of the opening of the tube can prevent the misplacing of the sampling swab. In addition, the bending mechanism is further disposed between the blocking portion and the position-limiting portion, so that the space for passing the external pipet therethrough is exposed only when the external pipet is entering and the blocking portion is bent. Therefore, the sample collection device of the present disclosure is advantageous for both the operator and the automated apparatus.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A sample collection device, comprising:
    a tube having an opening for receiving a sampling swab;
    a closure engaged with the tube for enclosing the opening; and
    a partitioning member disposed in the tube and the partitioning member comprising:
    a blocking portion disposed close to the opening for covering a portion of the opening so as to leave another uncovered portion of the opening as an entrance for passing the sampling swab therethrough; and
    a position-limiting portion connected with the blocking portion and extended into the tube for limiting the sampling swab in a space corresponding to the entrance inside the tube after the sampling swab passes through the entrance,
    wherein the partitioning member further comprises a bending mechanism disposed between the blocking portion and the position-limiting portion, so that the blocking portion is able to bend toward the position-limiting portion for exposing the covered portion of the opening when an external pipet enters the tube.

2. The sample collection device as claimed in claim 1, wherein the bending mechanism comprises a bending line for guiding a bending of the blocking portion.

3. The sample collection device as claimed in claim 1, wherein the bending mechanism comprises a bending gap for providing a deformation space for the blocking portion to bend toward the position-limiting portion.

4. The sample collection device as claimed in claim 1, wherein the position-limiting portion further comprises a hollow portion for receiving a portion of the blocking portion in a bent state.

5. The sample collection device as claimed in claim 1, wherein the position-limiting portion is a sheet structure having a length extended in a direction substantially parallel to a longitudinal direction of the tube.

6. The sample collection device as claimed in claim 5, wherein a length of the position-limiting portion is less than a length of the tube in the longitudinal direction, and a bottom edge of the position-limiting portion is a distance away from a bottom portion of the tube.

7. The sample collection device as claimed in claim 1, wherein the blocking portion is a plate structure, and the blocking portion and the position-limiting portion are substantially perpendicular to each other.

8. The sample collection device as claimed in claim 1, further comprising two engaging elements fixed in the tube and abutting against the position-limiting portion so as to position the partitioning member within the tube.

9. The sample collection device as claimed in claim 1, wherein the tube comprises an orientation structure for providing an orientation function as the tube is placed vertically.

10. The sample collection device as claimed in claim 1, wherein the closure comprises a first end and a second end, the first end is screwed with the opening of the tube and the second end is screwed with an automated opening and closing device, and the first end and the second end have opposite screwing directions.

11. The sample collection device as claimed in claim 1, wherein the tube has a protrusion disposed on an outer sidewall near the opening, and the closure has a recess corresponding to the protrusion so as to provide a notification as a screwing between the closure and the tube is completed.

* * * * *